United States Patent
Ivanov et al.

(10) Patent No.: US 7,591,964 B2
(45) Date of Patent: Sep. 22, 2009

(54) ELECTROCHEMICAL DEVICES COMPRISING PROTON CONDUCTING MEDIUMS

(75) Inventors: Sergei Vladimirovich Ivanov, Schnecksville, PA (US); William Jack Casteel, Jr., Fountain Hill, PA (US); Guido Peter Pez, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 6 days.

(21) Appl. No.: 11/952,437

(22) Filed: Dec. 7, 2007

(65) Prior Publication Data

US 2008/0090132 A1    Apr. 17, 2008

Related U.S. Application Data

(62) Division of application No. 10/910,529, filed on Aug. 3, 2004, now Pat. No. 7,419,623.

(51) Int. Cl.
*H01B 1/00* (2006.01)
(52) U.S. Cl. .................. 252/500; 423/276; 429/102; 429/105; 204/296; 568/3
(58) Field of Classification Search .................. 252/500; 568/3; 204/296; 423/276; 429/102, 105
See application file for complete search history.

(56) References Cited

U.S. PATENT DOCUMENTS 3,551,120 A    12/1970   Miller et al (Continued)

FOREIGN PATENT DOCUMENTS

WO    9960587    11/1999

OTHER PUBLICATIONS

J.O.M. Bockris, et al; Surface Electrochemistry; Plenum Press, p. 887.

(Continued)

*Primary Examiner*—Mark Kopec
*Assistant Examiner*—Khanh Tuan Nguyen
(74) *Attorney, Agent, or Firm*—Michael K. Boyer

(57) ABSTRACT

An electrochemical device and a proton conducting medium for use in an electrochemical device having a proton conducting electrolyte comprising the formula:

$$H_a M_b Q \cdot n H_2 O$$

where H is a proton, M is a cation, Q is the fluoroborate or fluoroheteroborate anion, n ranges from 0.01 to 1000, a ranges from 0.01 to 2 and b ranges from 0 to 2, a and b are chosen to render the formula electrically neutral, and when b is greater than 0, the ratio of b to a is less than 100 to 1.

21 Claims, 8 Drawing Sheets

U.S. PATENT DOCUMENTS

| | | | |
|---|---|---|---|
| 4,045,339 | A | 8/1977 | Korenowski et al. |
| 5,344,722 | A | 9/1994 | Bjerrum et al. |
| 5,470,677 | A | 11/1995 | Wiliams et al. |
| 5,525,436 | A | 6/1996 | Savinell et al. |
| 6,059,943 | A | 5/2000 | Murphy et al. |
| 6,130,357 | A * | 10/2000 | Strauss et al. ............ 568/3 |
| 6,180,829 | B1 | 1/2001 | Strauss et al. |
| 6,335,466 | B1 | 1/2002 | Strauss et al. |
| 6,448,447 | B1 | 9/2002 | Strauss et al. |
| 6,468,684 | B1 | 10/2002 | Chisholm et al. |
| 6,645,903 | B2 | 11/2003 | Strauss et al. |
| 6,781,005 | B1 | 8/2004 | Casteel, Jr. |
| 7,282,293 | B2 | 10/2007 | Ren et al. |
| 2004/0002002 | A1 | 1/2004 | Mizuta et al. |
| 2005/0181254 | A1 | 8/2005 | Uensal et al. |
| 2005/0227143 | A1 | 10/2005 | Amine et al. |
| 2006/0166067 | A1 | 7/2006 | Kiefer et al. |
| 2007/0048605 | A1 | 3/2007 | Pez et al. |

OTHER PUBLICATIONS

Yang, C, et al; Approaches and Technical Challenges to High Temperature Operation of Proton Exchange Membrane Fuel Cells:, Journal of Power Sources, 103;(2001) pp. 1-9.

Rupich, et al; "Characterization of Chloroclosoborane Acids as Electrolytes for Acid Fuel Cells", J. Electrochem Cos., Fol. 132, (1985); pp. 119-122.

Ivanov, et al; Synthesis and Stability of Reactive Salts of Dodecafluoro-closo-dodecaborate(2-), J. American Chemical Society, 2003, vol. 125, No. 16; p. 4694-4695.

S. Mori, et al; Chemical Properties of Various Organic Electrolytes for Lithium Rechargeable Batteries. . . 1. Characterization of Passivating Layer Formed on Graphite in Alkyl Carbonate Solutions,: Journal of Power Sources, 68, (1997); p. 59-64.

Aurbach, D., et al; Recent Studies on the Coorelation Between Surface Cemistry Morphology, Three-Dimentsional Structures and Peformance of Li and Li-C intercalation Anodes in Several Important Electrolyte Systems, : Journal of Power Sources 68, (1997) pp. 91-98.

Flandrois, S. et al; Carbon Materials for Lithium-ion Rechargeable Batteries,: Carbon 37, (1999); p. 165-180.

Ivanov s v et al: "Highly Fluorinated Weakly Coordinating Monocarborane Anions. 1-H-CB11F11-, 1-CH3-CB11-, And the Structure of (N(N-Bu)4)2(CuCl(CB11F11))" STN Caplus, 1998, XP002951158-abstract.

Lomme P et al: Opening of the Aza-Closo-Dodecarborane Skeleton by Bases: Stn Caplus, 1996, XP002951157 abstract.

Ivanov S V et al. Regioselective Fluorination of CB11H12-, New Weakly Coordinating Anions: Inorganic Chemistry, American Chemical Society, Easton, US, vol. 34, No. 26, Dec. 1995, pp. 6419-6420, XP002914225 ISSN: 0020-1669.

Ivanov S V et al. "Reactions of CB9H10- With Electrophiles, Including the Regioselective Mono- and Dihalogenation of The Lower Belt"; Inorganic Chemistry, American Chemical Society, Easton, US; vol. 35, No. 26, Dec. 1996, pp. 7882-7891, XP002914224; ISSN: 0020-1669.

Ivanov S V et al: Fluorination of B10H102- With an N-Fluoro Reagent. A New Way to Transform B-H Bonds into B-F Bonds: Inorganic Chemistry American Chemical Society, Easton, US, vol. 35, No. 24, 1996, pp. 6914-6915, XP001079910; ISSN: 0020-1669.

Iwahara, H.: "Fuel -cells, steam-electrolysis for hydrogen production and hydrogen separation using high temperature protonic conductors;" Devoces; Cambridge University Press; p. 511-522.

Haile, Sossina, et al; "Solid acids as fuel cell elecrolytes;" Materials Science, Nature, vol. 410, 2001, pp. 910-013.

Miura, Norio, et al; "Solid state gas sensors operating at room temperature;" Devices; pp. 527-538.

Staudt, Rhonda, et al; "IV.B.4 "Development of Polybenzimidazole-based, high-temperature Membrane and Electrode Assemblies for Stationary and Automotive Applications, DOW Hydrogen Program, FY2004 Progress Report; - 325-329.

Albert, G et al; "Solid State Protonic conductors, Present Main Applications and Future Prospects", Solid State Ionics,;145 pp. 3-16 (2001).

* cited by examiner

ELECTROCHEMICAL DEVICES COMPRISING PROTON CONDUCTING MEDIUMS

This application is a Divisional of U.S. patent application Ser. No. 10/910,529 filed 3 Aug. 2004, the entire disclosure of which is incorporated by reference herein in its entirety.

BACKGROUND OF THE INVENTION

Proton exchange fuel cells, including polymer electrolyte membrane fuel cells, offer clean and efficient energy conversion for power generation by converting chemical energy into electrical energy. Electrochemical conversion is effected by introducing an oxygen-containing oxidant gas through a gas diffusion cathode and introducing a hydrogen-containing fuel gas through a gas diffusion anode. Protons migrate into a proton conducting electrolyte medium containing a proton conductor and react with reduced oxygen to form water. To facilitate chemical conversion, platinum containing electrodes are generally employed.

Several types of fuel cells have been developed based on the type of the fuel employed, e.g., hydrogen, natural gas, gasoline, and alcohols; their operating conditions, e.g., low or high temperature; and the type of proton conducting electrolyte used in the fuel cell. Examples of fuel cells include the alkaline fuel cell, polymeric-electrolyte-membrane (PEM) fuel cell, phosphoric acid fuel cell, molten carbonate fuel cell, and solid-oxide fuel cells.

Low temperature operation of a fuel cell (<100° C.) typically requires using very pure hydrogen as the hydrogen source. However, this source is relatively expensive and requires complex hydrogen storage devices. Hydrogen from carbon based fuels, e.g., that which comes from the water-gas-shift reaction $$CO + H_2O \Leftrightarrow CO_2 + H_2$$

is less costly and easier to store. However, such fuel sources contain various amounts of carbon monoxide, and at <100° C. a 10 ppm level of carbon monoxide may poison the platinum catalyst at the cathode and anode via adsorption. Higher temperature operation of proton membrane exchange fuel cells (at least 100 to 250° C.) significantly reduces the effect of carbon monoxide adsorption. Higher temperature may also improve reaction kinetics and efficiency of the fuel cell.

Higher temperature operation of fuel cells creates significant challenges in fuel cell design. One of these challenges is in the selection of the proton conducting electrolyte. Proton conducting media employed in fuel cells operating at high temperature should have one or more of the following: high conductivity, good chemical, electrochemical, and morphological stability, oxidation resistance, good hydrogen and oxygen solubility, and an optimal interaction with the electrode catalyst material(s).

The hydrated perfluorinated sulfonic acid polymer, such as, Nafion™ (a trade mark of DuPont), and similar materials that are also commercially available, are commonly used as proton conducting electrolytes for low temperature fuel cell operation. However, because the proton-conduction mechanism in Nafion™-type membranes is based on the migration of hydrated protons, fuel cells using Nafion™-type membranes require a complicated water management system and pressurized operation above 100° C. Phosphoric acid cells offer an opportunity to operate fuel cells at high temperature but the phosphate anions are strongly absorbed on the platinum catalyst. A proton conducting electrolyte having strong adsorption characteristics in the platinum catalyst results in a loss of active sites for oxygen reduction, and a correspondingly low current density, lowering the power density of the fuel cell.

The following patents and articles are representative of the state of the art with respect to proton conducting membranes for use in fuel cells and electrochemical devices.

U.S. Pat. No. 6,468,684, discloses solid acid electrolytes of the general formula $M_aH_b(XO_t)_c$ where H is a proton, M is a metal such as Li, Be, Na, and Mg, X is Si, P, S, As and a, b, c, and t are rational numbers, for use as proton conducting materials. These electrolytes do not require hydration and can be operated at temperatures above 100° C. Composite membranes fabricated from the solid acid, $CsHSO_4$, a representative of this class show conductivities as high as 8 mS cm$^{-1}$ at 146° C. in humidified air ($p_{H_2O}$=3.13×10$^{-2}$ atm).

U.S. Pat. No. 5,344,722 discloses a phosphoric acid fuel cell in which the electrolyte includes phosphoric acid and a fluorinated compound, such as a salt of nonafluorobutanesulphonate or a silicone compound such as polyalkylsiloxane, e.g., polymethylsiloxane.

It is reported in *Surface Electrochemistry* J. O. M. Bockris and S. U. M. Khan, Plenum Press, p 887 that aqueous solutions of trifluoromethanesulfonic acid show a higher oxygen reduction rate on a platinum catalyst than solutions of phosphoric acid, presumably because of an improved oxygen solubility in the electrolyte and a lower adsorption of the acid at the Pt catalyst surface.

Alberti, et al in the article entitled, *Solid State Protonic Conductors, Present Main Application and Future Prospects*, Solid State Ionics, 145 (2001) 3-16 disclose a wide variety of proton conducting membranes for fuel cells. Examples of proton conducting materials include proton-conducting polymers impregnated with hydrophilic additives, such as heteropolyacids, zirconium phosphate, sulfated zirconia; sulfonated polyether ketones; and solid acid electrolytes, such as perfluorinated sulfonic acid polymers.

Yang, et al, in the article, *Approaches And Technical Challenges To High Temperature Operation Of Proton Exchange Membrane Fuel Cells*, Journal of Power Sources, 103, (2001), 1-9 disclose fuel cells employing a platinum anode catalyst. Composite membranes based upon perfluorinated sulfonic acids (Nafion™) and zirconium hydrogen phosphate as well as imidazole/Nafion membranes are mentioned.

U.S. Pat. No. 6,059,943 discloses solid-state, inorganic-organic composite membranes useful as ionically conducting membranes in electrochemical devices. Examples are based upon oxidation resistant polymeric matrices filled with inorganic oxide particles. Organic polymers include polytetrafluoroethylene, perfluorosulfonic acid, polysulfones and the like, while inorganic oxides are based upon heteropolytungstates, heteropolymolybdates, anions of tantalum and niobium, etc.

Rupich, et al in the article entitled *Characterization of Chloroclosoborane Acids as Electrolytes for Acid Fuel Cells*, J. Electrochem. Soc. 1985, 132, 119 disclose hydrated chloroclosoborane acids, $H_2B_{10}Cl_{10}$ and $H_2B_{12}Cl_{12}$ as alternative liquid electrolytes for intermediate temperature fuel cells. As described in this reference, aqueous solutions of these acids also show poor oxidative stability and a stronger adsorption on the Pt catalyst than aqueous solutions of sulfuric acid which itself adsorbs strongly on the Pt cathode.

All the patents cited above are incorporated herein by reference.

BRIEF SUMMARY OF THE INVENTION

The invention provides proton conducting mediums comprising proton conducting electrolytes for electrochemical devices (e.g. for fuel cells) comprising a fluoroborate or fluoroheteroborate of the formula:

$$H_aM_bQ.nH_2O$$

where H is a proton, M is a cation, Q is the fluoroborate or fluoroheteroborate anion; and n molecules of water of hydration ($H_2O$), which can be any number, or in the range from 0.01 to 1000, a ranges from 0.01 to 2, b ranges from 0 to 2, and the ratio of b to a is less than 100 to 1. The anion may be monovalent or divalent, the cation may have an oxidation state ranging from +1 to +4; from this (and considering the +1 charge on the proton, whether free or solvated), the subscripts a and b are so chosen to render the formula electrically neutral. As written the formula describes an acid salt when b is greater than 0, but this invention includes when there is no cation in the formula (i.e. when b=0). For the embodiments when b is 0, a=1 or 2 (i.e. Q is a monovalent or divalent anion), respectively; the formula composition is then that of a hydrated acid, $H_aQ.nH_2O$. When b is greater than 0, the proton conducting electrolyte is an acid salt, $H_aM_bQ.nH_2O$. The proton conducting electrolytes of this invention also include mixtures of the acid $H_aQ.nH_2O$, and the acid salt, $H_aM_bQ.nH_2O$ for which Q may be the same or different, or mixtures of the same or different acid salts, $H_aM_bQ.nH_2O$, (M and/or Q may be the same or different) or any combination of the above. For mixtures of hydrated acids of this invention, the average value for a will range from 1 to 2.

The proton may be free (as $H^+$) or solvated with one or more water molecules e.g., as the hydroxonium ion, $H_3O^+$. M is any cation which is stable over the electrochemical window of the fuel cell. Thus M should be resistant to reduction by hydrogen at the fuel cell's anode and to oxidation by oxygen at the fuel cell's cathode.

Suitable cations are those of the Alkali Metals (Group 1 of the Periodic Table), such as, Li, Na, K, Rb, Cs and Alkaline Earth (Group 2 of the Periodic Table), such as, Be, Mg, Ca, Ba, Sr, and cations of the Group 3 (of the Periodic Table) and Lanthanide series (of the Periodic Table) elements, such as, Al, Sc, Y, La, Ce. Additionally, ammonium and organic substituted ammonium cations, which are also relatively oxidation and reduction resistant may be used. Examples of organic ammonium cations useful in this invention include tetraethylammonium, tetrabutylammonimum, triethylammonium, monomethylammonium, dimethylammonium, trimethylammonimum, tetramethylammonium, imidazolium, and n-alkyl imidazolium.

The hydrated acid, $H_aQ.nH_2O$ having (hydrated) protons as the only cations may be expected to offer the highest conductivity. The introduction of other acid cations however, provides a wide measure of control over the physical properties (and to some extent, the conductivity) of the system particularly its melting point and therefore the physical state of the proton conducting electrolyte at the fuel cell's operating conditions.

The anion Q may be a polyhedral fluoroborate or fluoroheteroborate, such as the examples compounds shown in FIG. 1. FIG. 1 shows examples of the polyhedral clusters having 12 and 10 vertices useful as the proton conducting electrolytes in the proton conducting mediums of this invention. Alternatively, the proton conducting electrolytes may be ten, eleven, or twelve atom polyhedral clusters comprising boron atoms alone or boron atoms with one carbon atom in the cluster's cage-like chemical structure. The polyhedral boron clusters may have fluorine, hydrogen, chlorine, bromine, atoms and/or —OR, where R is H, an alkyl or fluoroalkyl group bonded to the boron atoms of the cluster. Included are three classes of anions:

(i) The closo-borate anion of composition $(B_{12}F_xZ_{12-x})^{2-}$ or $(B_{10}F_xZ_{10-x})^{2-}$ where Z is H, Cl, Br or OR, where R is H, alkyl or fluoroalkyl, and x, on an average basis, ranges from 3 to 12, and 2 to 10, respectively;

(ii) The *closo*-ammonioborate anion compositions of formula $((R'R''R''')NB_{12}F_xZ_{(11-x)})^{1-}$ or $((R'R''R''')NB_{10}F_xZ_{(9-x)})^{1-}$, where N is bonded to B and each of R', R'', R''' is independently selected from the group consisting of hydrogen, alkyl, cycloalkyl, aryl and a polymeric group; Z is H, Cl, Br, or OR, where R is H, alkyl or fluoroalkyl, and x, on an average basis, ranges from 0 to 11, or 0 to 9, respectively.

(iii) The *closo*-monocarborate anion compositions of formula $(R''''CB_{11}F_xZ_{(11-x)})^{1-}$ or $(R''''CB_9F_xZ_{(9-x)})^{1-}$, where R'''' is bonded to C and selected from the group consisting of hydrogen, alkyl, cycloalkyl, aryl, and a polymeric group, Z is H, Cl, Br, or OR, where R is H, alkyl or fluoroalkyl, and x, on an average basis, ranges from 0 to 11, or 0 to 9, respectively.

In one embodiment the invention is a fuel cell comprising a hydrogen anode, an oxygen cathode, and the proton conducting medium comprising a proton conducting electrolyte comprising the above-described fluoroborates or fluoroheteroborates.

The chemical stability of the polyhedral fluoroborate acids and acid salts of composition $H_aM_bQ.nH_2O$ make them useful as proton conducting electrolytes in electrochemical devices at any temperature or at temperatures from 80-300° C. or 120-250° C. The proton conducting mediums of this invention are useful in electrochemical devices, such as, fuel cells, water or steam electrolyzers for the production of hydrogen and oxygen—essentially fuel cells operating in reverse, and electrochemical $H_2$ sensors which function by measuring an $H_2$ (gas)/$H^+$ (solid or liquid) electrochemical potential. The proton conducting mediums of this invention comprising the fluoroborate acids and acid salts and/or fluoroheteroborate acids and acid salts provide a useful combination of physical, electrical and chemical properties. The compositions can function as either solid or liquid proton conducting electrolytes, at a range of humidity levels, and temperatures including low temperatures, from about ambient to moderate temperatures of up to about 250° C. and higher temperatures. They are suitable as proton conducting electrolytes for ($H_2/O_2$) fuel cells that operate at the temperature range of from 80° C. to 250° C., or higher temperatures of this range from 150° C. to 250° C. where an $O_2$ electrode is more efficient and where the cell is less sensitive to CO poisoning. Some embodiments of the proton conductor electrolytes of this invention have a high conductivity, an affinity for water, a resistance to reduction (by $H_2$) and oxidation (by $O_2$). Those results are seen for those embodiments when the proton conducting electrolytes are liquids or solids. Some embodiments of the proton conducting electrolytes of this invention are better solvents for oxygen than the currently used fuel cell liquid electrolyte ($H_3PO_4$) and have better electrochemical properties than $H_3PO_4$, allowing for the attainment of higher current densities and the construction of high power density fuel cells.

DETAILED DESCRIPTION OF THE INVENTION

Figure 1:
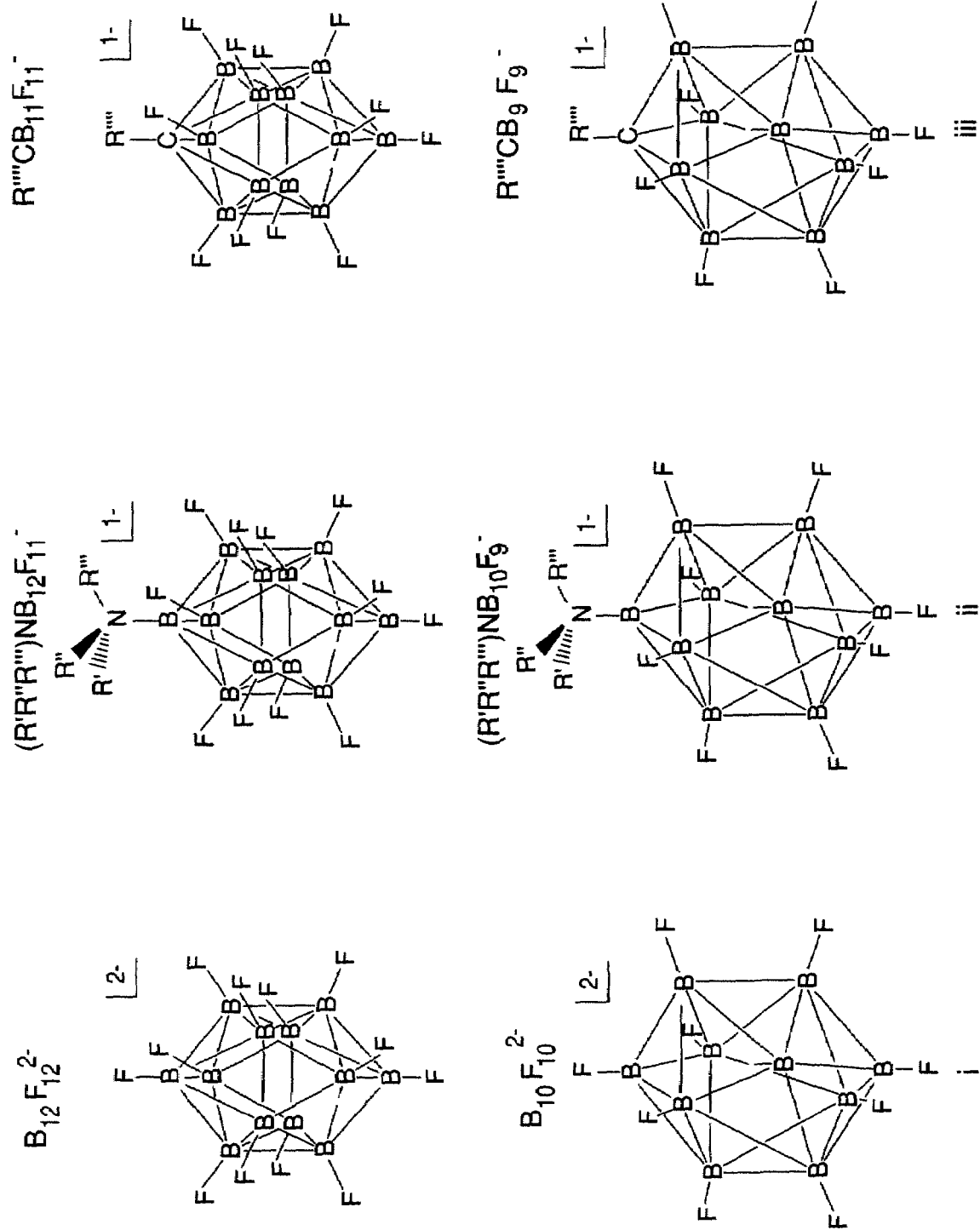
FIG. 1 shows chemical structures of fluorinated closoborate structures shown in column (i), closo-ammonioborate structures shown in column (ii), and closo-monocarborate structures shown in column (iii) useful in the electrochemical devices/proton conducting mediums of this invention. Note, that fluorine atoms (F) shown can be substituted with other groups (Z), which include hydride, other halogens, hydroxyl, alkoxy groups, and other groups as described herein.

Related applications assigned to the assignee of this application include U.S. Ser. Nos. 60/561,193; 10/655,476 and 10/427,341, that are incorporated in their entireties herein by reference.

The term "alkyl" will be used herein to mean a paraffinic hydrocarbon group which may be derived from an alkane by dropping one hydrogen from the formula. Examples are methyl ($CH_3$—), ethyl ($C_2H_5$—), propyl ($CH_3CH_2CH_2$—), isopropyl (($CH_3)_2CH$—), and tertiary butyl (($CH_3)_3C$—). The alkyl groups may have any number of carbons, or 1-10 carbons. The alkyl groups can be branched, straight chains, or comprise ringed structures. The term "cycloalkyl" may be used herein to describe an alkyl having at least one ring in the structure, although cycloalkyl is included in the term "alkyl" unless alkyl is described as only branched or straight-chained. The cycloalkyl group can have any number of carbons, or 4 to 10 carbons, or 4 to 7 carbons.

The term "aryl" will be used herein to mean phenyl, benzyl, naphthyl, cyclopentyl, fluorenyl, or tolyl.

The term "fluoroalkyl" will be used herein to mean the alkyl group as defined above wherein at least one H is substituted with a fluorine. Highly fluorinated fluoroalkyl groups are alkyl groups in which sixty percent or more, up to one hundred percent (fully fluorinated) of the hydrogens have been substituted by fluorine.

The term "polymeric group", when used to describe the substituent groups of the fluoroborate or fluoroheteroborate acids or acid salts of this invention, means a polyolefin, polyether, or polyamide, or an aryl- or alkyl-substituted polyolefin, polyether, or polyamide.

The terms "proton conducting membrane", or "proton conducting medium" may be used interchangeably; however, the use of the term proton conducting membrane is not meant to be limiting, and it is understood that the proton conducting medium may be in the form of a membrane, or it may be a liquid, a gel, a solid, a mixture of a solid and a liquid, or it may take any form. The terms "proton conductor", or "proton conducting electrolyte" may be used interchangeably.

The invention relates to a proton conducting electrolyte useful in a proton conducting medium in an electrochemical devices, e.g. fuel cells. In addition to the proton conducting medium of this invention, electrochemical devices of this invention typically comprise an anode, e.g. a hydrogen anode, a cathode, e.g. an oxygen cathode and a solid or liquid proton conducting electrolyte. The proton conducting electrolyte comprises a hydrated fluoroborate or fluoroheteroborate acid or acid salt represented by the formula:

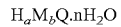

where H is a proton, which is associated with n molecules of water of hydration ($H_2O$), M is a cation, and Q is a fluoroborate or fluoroheteroborate anion. The anion may be monovalent or divalent, the cation may have an oxidation state ranging from +1 to +4; from this (and considering the +1 charge on the proton, whether free or solvated), the subscripts a and b are so chosen to render the formula electrically neutral; therefore, a can be a real number from 0.01 to 2 and b can be a real number from 0 to 2 and when b is greater than 0, the ratio of b to a is less than 100 to 1. Included is the embodiment where there is no cation in the formula (b=0), in which case a=1 or 2 (when Q is a monovalent or divalent anion, respectively) thereby the formula is for a fluoroborate or fluoroheteroborate acid, $H_aQ \cdot nH_2O$. Also included is the embodiment where the proton conducting electrolyte comprises a mixture of this acid $H_aQ \cdot nH_2O$ and the acid salt, $H_aM_bQ \cdot nH_2O$. The molar proportions of the acid and acid salt may range from 1:10 to 100:1 of the acid to the acid salt, or from 1:1 to 10:1 of the acid to the acid salt.

The proton may be free (as $H^+$) or solvated with one or more water molecules, e.g. as the hydroxonium ion, $H_3O^+$.

M is any cation which is stable over the entire electrochemical window of the electrochemical device. Thus, in most embodiments, M should be resistant to reduction by hydrogen at the electrochemical device's (e.g. the fuel cell's) anode, and to oxidation by oxygen at the electrochemical device's (e.g. the fuel cell's) cathode. The tabled electrochemical reduction potentials (E°) as in the CRC Handbook of Chemistry and Physics, D. R. Lide (Ed) 74th Ed. pages 8-21 to 8-31, may be used as an approximate guide (not a definitive test) for choosing an appropriate cation. Thus a suitable cation may be one where (a) its reduction to a lower oxidation state has a lower (more negative) E° than that of the standard hydrogen electrode: E° for $2H^+ + 2e^- = H_2$ is 0 V and (b) an oxidation of the cation to a higher valent state with oxygen is precluded with cations for which E° for the corresponding higher valent state is higher (more positive) than that for the reduction of oxygen in acid media: $O_2 + 4H^+ + 4e^- = 2H_2O$ for which E°=1.229V. Examples are the monovalent and divalent cations respectively of Groups 1 and 2 of the Periodic Table, eg. $Li^+$, $Na^+$ (for $Na^+ + e^- = Na$, E° is −2.71 V) Mg, Ca (for $Ca^{2+} + 2e^- = Ca$, E° is −2.87 V) also the trivalent cations of Group 13, $Al^{3+}$ (for $Al^{3+} + 3e^- = Al$, E°=−1.67V), and $Ga^{3+}$ etc.

Higher valent cations of Groups 1 and 2 are not known and would be expected to have even more negative E° values thus satisfying criterion (b). Other cations from other Groups of the Periodic Table that satisfy both criteria are the cerium (+3) ion: E° for $Ce^{3+}+3e^-=Ce$ is −2.34V and E° for $Ce^{4+}+e^-=Ce^{3+}$ is 1.72V; and cobalt (+2): E° for $Co^{2+}+2e^-=-0.28V$ and for $Co^{3+}+e^-=Co^{2+}$, E°=1.92V; zirconium (+4) ion: E° for $Zr^{4+}+4\,e^-=Zr$ is −1.45 V; hafnium (+4) ion, E° for $Hf^{4+}+4\,e^-=Hf$ is −1.55V; nickel (+2) ion, E° for $Ni^{2+}+2\,e^-=Ni$ is −0.257V, and for $Ni^{2+}+2H_2O=NiO_2+4H^++2\,e^-$ is 1.678 V; and lanthanum (+3) ion, E° for $La^{3+}+3\,e^-=La$ is −2.379 V. However cations that do not satisfy both criteria may be useful as the cation M in the proton conducting electrolyte.

Tertiary and quaternary alkyl or mixed alkyl, aryl ammonium ions of formula $R^*_3NH^+$ and $R^*_4N^+$ respectively, are relatively reduction and oxidation resistant and would therefore also be useful as the (monovalent) cations of the proton conducting electrolyte. R* is any alkyl, phenyl or alkyl substituted phenyl group.

Alternatively, a combination of two or several different cations could be employed as the cation M for the proton conductor, eg. $Li^+K^+$, $Ca^{2+}Li^+$ and so on. While the presence of the cation is not necessary for protonic conduction, it provides a means of controlling hydration of the fluoroborate or fluoroheteroborate acid salt used in the electrochemical device of this invention and this is particularly true for the smaller (more Lewis acidic) cations, i.e. $Li^+$, which can tightly coordinate water. The hydration is useful in some embodiments for maintaining liquidity (when this is desired) and may assist in proton transfer, by providing proton conductivity pathways in the proton conducting electrolyte. The larger (higher radius to charge ratio) less hydrophilic cations (e.g. $Cs^+$) will tend to raise the melting point of the acid salt and yield compositions that are solid state protonic conductors having decreased liquidity which may be particularly useful for other embodiments, such as non-stationary fuel cells, such as automotive fuel cells.

The group Q may be selected from the fluoroborate (i) and heterofluoroborate (ii) and (iii) anions shown in FIG. 1 or similar fluoroborate and heterofluoroborate anions to those shown in FIG. 1. Q may be selected from the following classes: (i) The closoborate anion compositions of formula $(B_{12}F_xZ_{(12-x)})^{2-}$, or $(B_{10}F_xZ_{10-x})^{2-}$ where Z is H, Cl, Br, or (OR), where R is H, alkyl or fluoroalkyl; x ranges, on an average basis, from 3 to 12, or from 2 to 10, respectively. The compositions are polyhedral clusters consisting of ten or twelve boron atoms where each boron is attached as defined to a hydrogen, a halogen atom, hydroxyl group, or alkoxyl group. Examples of these fluoroborate anions, as components of specific salts, $M_bQ$ and of the corresponding acids $(H_aM_bQ)$ and the methods of making them are described in U.S. Pat. No. 3,551,120; Solntsev, K. A.; Mebel, A. M.; Votinova, N. A.; Kuznetsov, N. J.; Charkin, D. P.; Koord. Khim. 1992, 18, 340; U.S. Pat. No. 6,448,447 B1; and U.S. Ser. No. 10/427,341, incorporated herein in their entireties by reference.

(ii) The c/oso-ammoniofluoroborate anion compositions of formula $((R'R''R''')NB_{12}F_xZ_{(11-x)})^{1-}$, or $((R'R''R''')NB_{10}F_xZ_{(9-x)})^{1-}$, where N is bonded to B and each of R', R'', R''' is independently selected from the group consisting of hydrogen, alkyl, cycloalkyl, aryl and a polymeric group, Z is H, Cl, Br, or (OR), where R is H, alkyl or fluoroalkyl; and x, on an average basis, ranges from 0 to 11, or from 0 to 9, respectively. These anion compositions are also polyhedral boron clusters of 10 or 12 boron atoms in which one of the borons is attached to an ammonia group (NR'R''R'''), with F, H, Cl, Br or OH groups attached to the remaining borons.

A further description of these compositions and examples thereof may be found in U.S. Pat. No. 6,335,466 B1, incorporated herein in its entirety by reference.

(iii) The closo-monocarborate anion compositions of formula $(R''''CB_{11}F_xZ_{(11-x)})^{1-}$ or $(R''''CB_9F_xZ_{(9-x)})^{1-}$, where R'''' is bonded to C and selected from the group consisting of hydrogen, alkyl, cycloalkyl, aryl, and a polymeric group; Z is H, Cl, Br, or (OR), where R is H, alkyl or fluoroalkyl; and x, on an average basis, ranges from 0 to 11 or from 0 to 9, respectively. These fluorinated closo-monocarborate anion compositions are also polyhedral clusters comprised of 11 or 9 borons and a single carbon atom. As defined above the borons are partially or fully fluorinated, and the carbon atom is connected to a single organic substituent group. Such anion compositions are described in U.S. Pat. No. 6,130,357, incorporated herein in its entirety by reference.

Examples of useful fluoroborate or fluoroheteroborate acids and acid salts in the proton conducting mediums of this invention include: $B_{12}F_{12}{}^{2-}$; $B_{12}F_xH_{12-x}{}^{2-}$ where x is 3 to 12, or 7 to 12, on an average basis; $B_{12}(OR)_xH_{12-x}{}^{2-}$ where R is an alkyl or fluoroalkyl and x is 3 to 12, or 7 to 12, on an average basis; $B_{12}F_{11}N(R'R''R''')^{1-}$ where R', R'', and R''' are independently alkyls, or are each ethyl; or $B_{12}F_xCl_{12-x}{}^{2-}$ or $B_{12}F_x(OR)_{12-x}{}^{2-}$ where x is 3 to 12, or 7 to 12, on an average basis.

Of the three borate anion classes listed above, structures of class (i) are divalent anions and provide more protons (a=2 in formula) as compared to a=1 for the anions of classes (ii) and (iii). Therefore the anions of class (i) (all else being equal) potentially will have higher proton conductivity as compared to the anions of the class (ii) and (iii). The anions of class (i) are synthesized by a person of ordinary skill in the art via known routes. For synthetic routes to polyhedral hydridoborates (fluorinated polyhedral borate precursors) see: "Polyhedral Boranes", E. L. Muefterties and W. H. Knoth, Marcel Dekker, Inc. NY 1968.

The heteroborates of classes (ii) and (iii) above have the advantage of being easily functionalized at their nitrogen and carbon atom sites respectively as described in U.S. Pat. No. 6,335,466 and U.S. Pat. No. 6,130,357 both incorporated herein by reference. Of the three classes, the fluorocarboranes (iii) are the most weakly coordinating anions from which follows that their protonated forms $(HQ.nH_2O)$ should be the strongest acids implying a higher mobility and therefore a higher conductivity for their (single) proton.

The acid salt of said formula $H_aM_bQ.nH_2O$ is associated with a variable number (n=1 to 1000) of water molecules of hydration. At both the anode and cathode of the fuel cell the acid salt will be in equilibrium with both liquid water and water vapor. Some retention of water may be necessary for providing a mechanism for proton transport and also to provide liquidity, if required. Reference: "Proton Conductors", P. Colomon Ed. Cambridge Univ. Press (1992), Chapter 2.

The proton conducting electrolytes, $H_aM_bQ.nH_2O$ can be either solid or liquid at the operating conditions of the device. The electrochemical device and/or the proton conducting medium may additionally comprise an inert porous support that functions as a membrane which separates the anode and cathode of the device. The inert porous support is more likely to be used in the electrochemical device when the proton conducting electrolyte is a liquid. A liquid proton conducting electrolyte is expected to be advantageous because of its expected higher conductivity due to an expected more facile proton transfer in a liquid medium. To achieve a liquid form, the hydrate level (n) is increased sufficiently to generate a liquid. Typically, when hydrogen is the only cation, that is when b is 0, n is at least 6, generally at least 8 and preferably at least 10 and can be up to 1000 depending on the electrochemical device's operating temperature and pressure. As described below, the presence of cations in addition to hydrogen (when b is greater than 0) will effect the melting point and the state of hydration.

Solid state proton conducting electrolytes have the advantage of providing, without the need of other components, the required physical separation between the electrochemical device's anode and cathode. Solid forms of the proton conducting electrolyte of the formula $H_aM_bQ.nH_2O$ can be used in fuel cells. Solid forms generally exist when n is less than 6. Solid proton conducting electrolytes can be obtained by doping the liquid forms of the proton conducting electrolyte of this invention, e.g. fluorododecaborate acids (where b is 0), with inorganic cations (e.g., $M=K^+$, $Ba^{2+}$, and/or any of the other cations previously listed.). The inorganic cations may be provided by adding the acid salts of $H_aM_bQ.nH2O$ where b is greater than 0, or gpure salts of anions Q, or other known sources of the cations, to form higher viscosity or solid proton conducting electrolyte compositions with higher melting points.

The polyhedral fluoroborate, $H_aM_bQ.nH_2O$ proton conducting electrolytes can be generated by a direct fluorination of the corresponding cluster borates, e.g. polyhedral hydridoborates in a liquid medium. Alternatively, the hydridoborate precursor of the neutral salt, $M_bQ$, can be fluorinated in a liquid medium and this followed by an acid metathesis. The replacement of the cation with a proton is described in Examples 3 to 5 below. A partial exchange of such a salt, $M_bQ.nH_2O$ with protons leads to the acid salt having the structure: $H_aM_bQ.nH_2O$. Other halogens, Cl and Br are introduced into the fluoroborates by a direct reaction of the latter with these elements.

In direct fluorination to make the proton conducting electrolyte of this invention, fluorine is diluted with an inert gas, e.g., nitrogen, to a concentration of from 10 to 40% by volume of the total gases. The liquid medium or carrier for the hydridodoborate salt is one that is not substantially reactive with fluorine. One conventional medium is liquid hydrogen fluoride, HF. Other liquid mediums can be used in the process and include water, organic acids such as formic acid, acetic acid, trifluoroacetic acid and the like. The acidity of the liquid medium, particularly the liquid medium employed in the fluorination of the hydridoborates, can affect the solubility of the precursor hydridoborates and the fluorinated hydridoborate salt and effect an acidity change therein. It is preferred that the medium be designed to maintain both the hydridoborates and the fluorinated hydridodoborate salt product in solution in the medium.

Radical scavengers can be used in the fluorination process to reduce byproduct formation and improve reaction efficiency. In aqueous solutions, radical scavengers appear to limit the formation of hydrogen peroxide, or HOF, which may be generated with fluorine. Radical scavengers are used where organic acids, such as formic acid, are used. The radical scavengers inhibit the side-reaction of fluorine with the solvent, thereby improving fluorination efficiency. Examples of radical scavengers include oxygen, and nitroaromatics. The introduction of a small amount of air to the liquid medium removes free radicals generated in the direct fluorination of the hydridodoborate salts.

Fluorination of the polyhedral hydridoborate anions can be carried out over a temperature range sufficient to maintain liquid phase conditions. For effecting the fluorination of the polyhedral borate anions the temperature is from −30 to 100° C., typically from 0 to 20° C. Pressures during fluorination are such as to maintain liquid phase conditions, typically atmospheric.

The extent of fluorination of the polyhedral hydridoborates and of the borate salts can be controlled by varying the reaction conditions and reagent stoichiometries. For the preparation of a mixed halogen fluoroborate (Q where Z is Cl or Br; or Cl or Br and H) the partially fluorinated product is reacted with $Cl_2$ or $Br_2$. Additional description and examples can be found in U.S. Pat. No. 3,551,120. Closo-borates comprising OH substituent groups can be prepared by treatment of a polyhedral hydro-c/oso-borate with 40% sulfuric acid as described in Peymann, T.; Knobler, C. B.; Hawthorne, M. F. Inorg. Chem. 2000, 39, 1163, incorporated herein by reference.

The hydrated fluoroborate acids $H_aQ.nH_2O$. (where n is at least 1, preferably at least 5, and more preferably n is at least 8 to 1000 can be formed from the fluoroborate salts. One method involves the treatment of an aqueous solution of the barium salts, BaQ or $BaQ_2$, or an aqueous solution of the calcium salts, CaQ or $CaQ_2$ with sulfuric acid, or with aqueous HF, and removing the insoluble salts, $BaSO_4$ and $CaF_2$ by filtration. Water is removed by distillation from the aqueous solution of the hydrated fluoroborate until the desired acid/water ratio is achieved.

As a proton conducting electrolyte for use in an electrochemical device, the fluoroborate or fluoroheteroborate acids or acid salts of the invention of the formula, $H_aM_bQ.nH2O$, can be used alone or in solutions, suspensions, or mixtures with one or more other fluoroborate or fluoroheteroborate acid or acid salts (having different M's and/or Q's) and/or they can be mixed to form a solution, suspension, or a mixture with other (types of) proton conducting electrolytes. Examples of other proton conducting electrolytes that can be combined with the proton conducting electrolytes of this invention include anhydrous phosphoric acid, alkane sulfonic acid, fluoroalkanesulfonic acid, or sulfuric acid, or combinations of the above to produce a desired proton conducting electrolyte. Fluoroborate or fluoroheteroborate acids or acid salts and phosphoric acid mixtures or other proton conducting electrolyte mixtures, whether the fluoroborate is in liquid or solid form, can be used within a compositionally wide range. Typical ratios in the proton conducting mediums are from 0.01:1 to 10:1 weight parts fluoroborate or fluoroheteroborate proton conducting electrolyte to weight parts phosphoric acid or other proton conducting electrolyte. Solid forms of the fluoroborate or fluoroheteroborate proton conducting electrolytes can be used as additives here for varying as desired, the melting points of these mixtures.

The fluoroborate and fluoroheteroborate acids and acid salts, as mixtures or alone (with or without other proton conducting electrolytes), can be blended with various polymers containing polar functional groups to form composite membranes that can be used as the proton conducting medium in an electrochemical device. The blending may be accomplished by imbibing the polymer with a solution of the fluoroborate or fluoroheteroborate acid and/or acid salt in solvent, e.g. polar organic solvent, for examples, N-methylpyrrolidone, or acetonitrile, and then at least partially removing the solvent from the resulting composite material. Or a polymeric film proton conducting electrolyte may be cast from a solution that contains both the polymer and one or more of the fluoroborate or fluoroheteroborate acids or acid salts (with or without other proton conducting electrolytes) in a mutual solvent. The polymers suited for forming composite membranes may include polymeric perfluorosulfonic acids, polyethylene oxide, polyimides, polysulfones. In general polymers that comprise carbonyl, amine, ether, sulfone or sulfoxide polar functional groups that may be expected to have an interaction with the proton or metal cation of the electrolyte may be used. Preferred are nitrogen or oxygen atom-containing polymers, such as polyvinylpyridine, polyaniline, polybenzimidazole, polybenzoxazoles and the like, where the interaction of the basic nitrogen or oxygen with the proton conductor is expected to facilitate the formation of a suitable blend of the two components. Additional examples of useful polymers are disclosed in U.S. Pat. No. 5,525,436.

The liquid proton conductoring electrolytes of this invention can be impregnated into a porous matrix, such as a porous matrix comprising microglass fibers, silicon carbide, boron nitride, or porous carbon materials, resulting in a proton conducting medium further comprising a separation membrane. Physical blends of the solid proton conducting electrolytes of this invention and a porous matrix, such as microglass fibers, silicon carbide, boron nitride, or porous carbon materials can also be employed in an electrochemical device.

The temperature range for operation of the electrochemical device can be any range, or 120-220° C., or 150-200° C.

The proton conductors of this invention may be used in any device in which $H_2$ (gas) is in an electrochemical equilibrium with a proton source. This is one of the elementary processes in a fuel cell. The proton conducting electrolytes can also be employed in hydrogen gas sensor devices where the $H_2$ partial pressure is a function of the measured potential of an electrode in contact with the proton conducting electrolyte. Additionally, the proton conductors are useful for the electrolysis of water to produce $H_2$ and $O_2$, optionally at higher temperatures in the presence of steam where higher electrochemical efficiencies may be realized; these devices here are essentially fuel cells in reverse. Reference: "Proton Conductors" ibid Chapter 32. For more information on fuel cells, and their components, see: Fuel cell handbook. By: A J Appleby; F R Foulkes. Publisher: New York: Van Nostrand Reinhold, ©1989.

The following examples are provided to illustrate various embodiments of the invention and are not intended to restrict the scope thereof.

EXAMPLE 1

Preparation of $[Et_3NH]_2B_{12}F_xH_{12-x}$ (x=10, 11, or 12)

A slurry of 2.01 g $K_2B_{12}H_{12}CH_3OH$ in 10 g glacial acetic acid was fluorinated at 20° C. with a gaseous mixture of 10% $F_2$/10%$O_2$/80% $N_2$ (% are by volume). A total of 116 mmol $F_2$ was added (22% excess). The slurry remained colorless throughout the fluorination and while its viscosity decreased complete dissolution of the solid was never observed. At the completion of the fluorination, the product slurry gave a negative iodide test for oxidizer. Solvents were then evacuated and the crude product dissolved in water. Triethylammonium hydrochloride (240 mmol) was added along with enough triethylamine to bring the solution pH up to 5. The product was filtered, washed with water and dried. 3.2 g (65% yield) of fluoroborate salts were isolated. 19F NMR analysis showed $B_{12}F_{10}H_2^{2-}$ (7%), $B_{12}F_{11}H^{2-}$ (18%), and $B_{12}F_{12}^{2-}$ (75%) with only traces of hydroxy-substituted impurities. The crude reaction product was dissolved in water and the pH of the solution adjusted to between 4-6 with triethylamine and triethylamine hydrochloride. The precipitated product was recrystallized, filtered and dried under vacuum at 100° C.

EXAMPLE 2

Fluorination of $K_2B_{12}H_{12}$ with Fluorine in Formic Acid (15% Loading; $O_2$ Added)

In this example, a colorless slurry containing 1.8 g (7.2 mmol) $K_2B_{12}H_{12}.CH_3OH$ in 10 ml formic acid was fluorinated at 0 to 10° C. as described in Example 1. A total of 108 mmol $F_2$ (25% excess) was added as 10% $F_2$/10% $O_2$/80% $N_2$. Over the course of the fluorination, the solids completely dissolved leaving a colorless, homogeneous solution at the completion of the fluorination. Analysis of the crude product solution by $^{19}F$ NMR revealed primarily $B_{12}F_{11}H^{2-}$ (35%), and $B_{12}F_{12}^{2-}$ (60%) and approximately 5% of the monohydroxy impurity $B_{12}F_{11}OH$. No dimer impurity was observed. Isolation of the product through the triethylammonium salt as above removed impurities and gave the above fluorinated borate cluster products in 80% yield.

EXAMPLE 3

Preparation of $H_2B_{12}F_{12}.nH_2O$ by direct fluorination of $H_2B_{12}H_{12}.nH_2O$ The fluorination of 2 weight % solution of $H_2B_{12}H_{12}.6H_2O$ in HF at about −15° C. with 20% $F_2$ in $N_2$ afforded $B_{12}F_{12}^{2-}$ with a very low content of the other anions (side-products). Based on the $^{19}F$ NMR spectrum of the crude reaction mixture, the molar ratio of the anions were: $B_{12}F_{12}^{2-}$ (1), $B_{24}F_{22}^{4-}$ (0.01), $B_{12}F_{11}(OH)^{2-}$ (0.05) and $BF_4^-$ (0.36). Approximately 3 mol % of $B_{12}H_{12}^{2-}$ has to decompose during the reaction to produce the molar ratio of $BF_4^-$ to $B_{12}F_{12}^{2-}$ 0.36. Thus, the yield of $H_2B_{12}F_{12}.nH_2O$ in the above reaction was close to 90%.

EXAMPLE 4

Preparation of Highly Fluorinated Hydroxy-Substituted Borate Cluster Salts

A colorless slurry containing about 4.0 g (17 mmol) of $K_2B_{12}H_{11}(OH)$ prepared as described in U.S. Pat. No. 3,551,120, incorporated herein above by a standard literature method, was dissolved in 15 ml formic acid and was treated with 10% $F_2$/10% $O_2$/80% $N_2$ (240 mmol $F_2$ total, 27% excess) at −10 to −5° C. Analysis of the crude product by $^{19}F$ NMR revealed primarily $B_{12}F_{11}(OH)^{2-}$ (55%), and $B_{12}F_{10}H(OH)^{2-}$ (35%) and approximately 5% of dihydroxy impurities.

EXAMPLE 5

Preparation of Highly Fluorinated Hydroxy-substituted Borate Cluster Salts

A colorless slurry containing 2.2 g (8.7 mmol) $K_2B_{12}H_{10}(OH)_2$, prepared as described in U.S. Pat. No. 3,551,120 was dissolved in 8 ml formic acid and treated with 10% $F_2$/10% $O_2$/80% $N_2$ (114 mmol $F_2$ total, 30% excess) at −10 to −5° C. Analysis of the crude product by $^{19}F$ NMR revealed primarily $B_{12}F_{10}(OH)_2^{2-}$ (30%), and $B_{12}F_9H(OH)_2^{2-}$ (60%) and approximately 10% of trihydroxy impurities.

EXAMPLE 6

Preparation of $(H_3O)_2B_{12}F_xH_{12-x}$, x=10, 11, or 12

A solid $Ba(OH)_2.8H_2O$ (2.53 g, 8.0 mmol) was added to a suspension of $[Et_3NH]_2[B_{12}F_{12}]$ (4.50 g, 8.0 mmol) in 50 ml of water, and triethylamine was distilled off under reduced pressure. As triethylamine was removed, an aqueous solution containing $BaB_{12}F_{12}$ was formed. This aqueous solution of $BaB_{12}F_{12}$ was treated with aqueous $H_2SO_4$, and $BaSO_4$ precipitate was removed by filtration. Water was distilled off from the filtrate, and the remaining solid was dried under vacuum at 190° C. for two hours.

The solid was analyzed by gravimetric analysis. The solid (0.211 g) was dissolved in 10 ml of water and treated with Ph$_4$PCl. The white precipitate that formed was washed with water and dried at 120° C. for 2 hours to collect 545.2 mg of [Ph$_4$P]$_2$[B$_{12}$F$_{12}$] (for H$_2$B$_{12}$F$_{12}$.2H$_2$O the collected amount of [Ph$_4$P]$_2$[B$_{12}$F$_{12}$] should be 550.5 mg, for H$_2$B$_{12}$F$_{12}$.4H$_2$O the collected amount of [Ph$_4$P]$_2$[B$_{12}$F$_{12}$] should be 504.6 mg). According to the gravimetric analysis, the composition of the solid acid was H$_2$B$_{12}$F$_{12}$.2H$_2$O. The IR spectrum of the fluorolube mull of the solid acid contains a broad intense OH stretch at 3084 cm$^{-1}$, a lower intensity OH stretch at 3269 cm$^{-1}$, and an HOH band at 1610 cm$^{-1}$, all attributive to (H$_3$O)$^+$ cation.

It is anticipated that a similar treatment of barium or calcium fluoroheteroborate salts with sulfuric acid can be used to generate hydrated acids of the heteroborates, e.g., H(R''''CB$_{11}$F$_x$Z$_{(11-x)}$).nH$_2$O and H((R'R'' R''')NB$_{12}$F$_x$Z$_{(11-x)}$.nH$_2$O.

The above described acid also can be produced by the common method for the preparation of acids with polyhedral borate anions, which includes eluting a salt of the anion via an ion-exchange column in H$^+$ form and removing water under reduced pressure. However, in contrast to the procedure of this example, that method may be time-consuming and may require evaporation of large amounts of water. It may also result in contamination of the product acids with organic impurities.

EXAMPLE 7

Determination of Stability of (H$_3$O)$_2$B$_{12}$F$_{12}$ Under Humid Air

Figure 3:
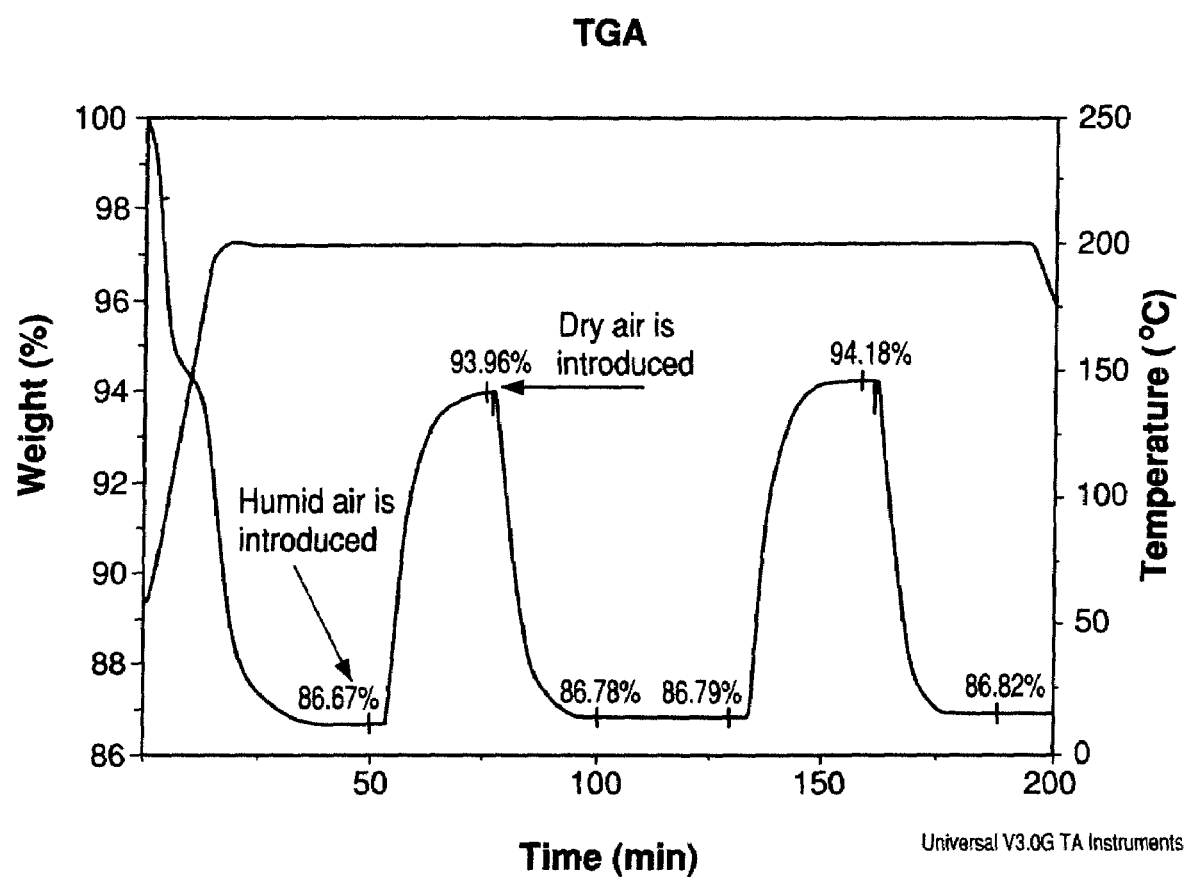
FIG. 3 shows a thermogravimetric analysis (TGA) of $H_2B_{12}F_{12} \cdot nH_2O$ at 200° C. under dry and humidified air flow.
Figure 4:
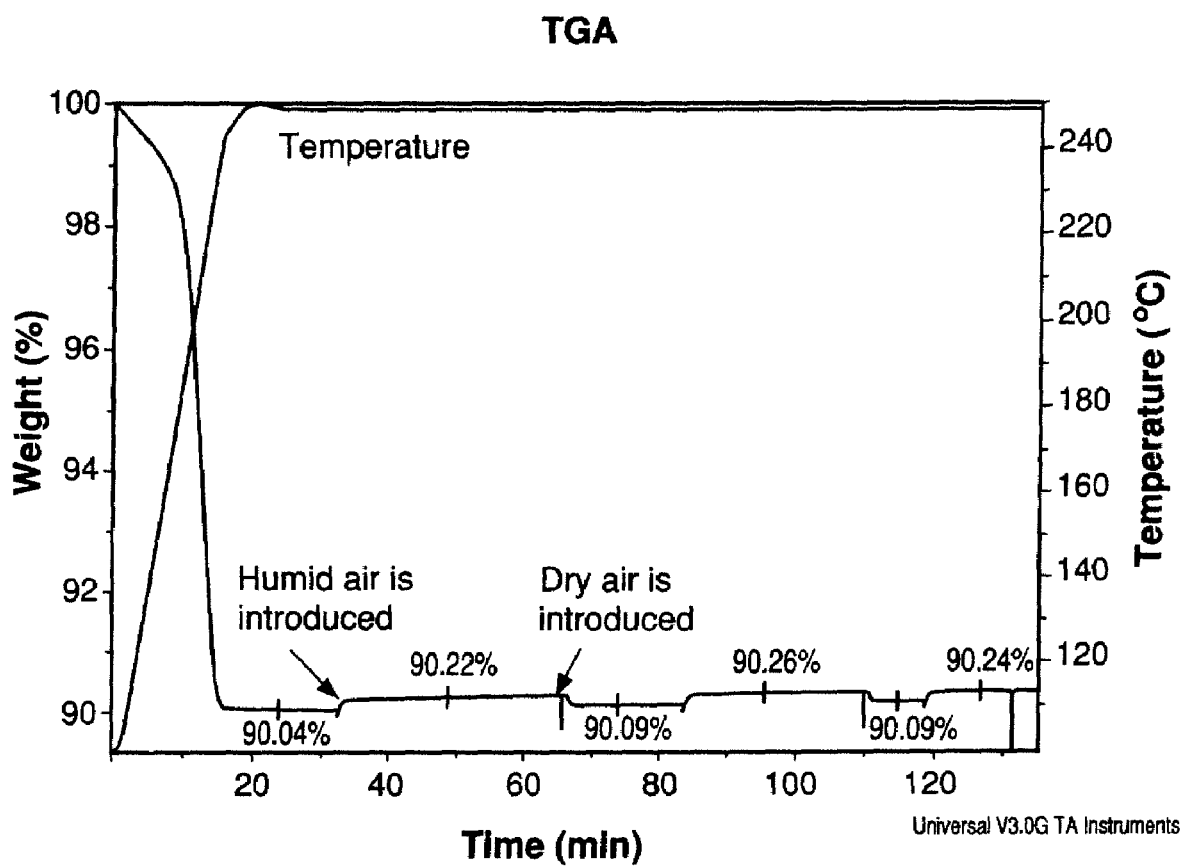
FIG. 4 shows a thermogravimetric analysis (TGA) of $H_2B_{12}F_{12} \cdot nH_2O$ at 250° C. under dry and humidified air flow.

This example shows that the acid, (H$_3$O)$_2$B$_{12}$F$_{12}$, is stable under humid air up to 250° C., under an inert atmosphere, and that the acid absorbs water at 250° C. under low water vapor pressure (in this case only 24 torr), an important feature in electrochemical devices, e.g. fuel cells. The solid acid prepared as above was exposed to air for 18 hours. Thermogravametric analysis (TGA) of the acid was performed under dry air. To determine water adsorption at these conditions, the airflow was switched between the dry air and the humid air (air bubbled through water at about 25° C.). The results of this test are shown in FIGS. 2-4.

Figure 2:
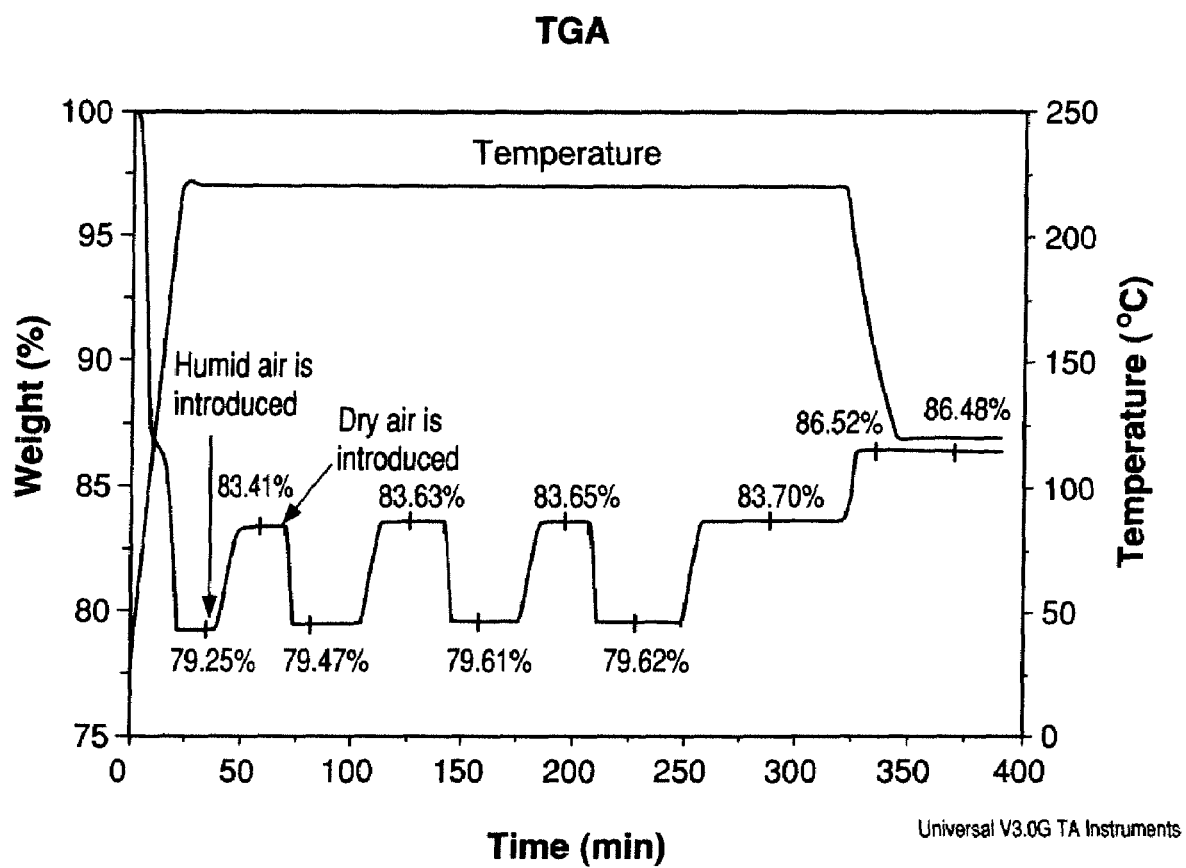
FIG. 2 shows a thermogravimetric analysis (TGA) of $H_2B_{12}F_{12} \cdot nH_2O$ at 220° C. under dry and humidified airflow.

As shown in FIG. 2, the results obtained upon heating from 25° C. to 220° C. under dry air atmosphere revealed that the solid lost 20.75% of its weight, which corresponds to a transformation between H$_2$B$_{12}$F$_{12}$.8H$_2$O to H$_2$B$_{12}$F$_{12}$.2H$_2$O. This composition was stable under an inert atmosphere at 220° C., but its composition changed to H$_2$B$_{12}$F$_{12}$.3.1H$_2$O at 24 torr of water vapor pressure (about 0.1% relative humidity). As shown in FIG. 4, the acid was also stable at 250° C., and it adsorbed much less water at this temperature. As shown in FIG. 3, at a temperature range from 120 to 200° C. and at a water vapor pressure of 24 torr, the composition of the solid acid was H$_2$B$_{12}$F$_{12}$.4H$_2$O. This solid composition did not show any weight loss when it was heated for ten hours at 200° C. under humid air.

Summarizing, there was essentially no weight loss of the composition under the test conditions, thus illustrating the acid's exceptional ability to retain water. Additionally, during the tests, the acid H$_2$B$_{12}$F$_{12}$.nH$_2$O showed no evidence of hydrolysis or decomposition.

EXAMPLE 8

Determination of the Stability of H$_2$B$_{12}$F$_{12}$.nH$_2$O Toward Hydrogen at High Temperatures The acid H$_2$B$_{12}$F$_{12}$.2H$_2$O, and a mixture of H$_2$B$_{12}$F$_{12}$.nH$_2$O (n less than 100) with 5% Pt on carbon (approximately 5/1 mass ratio) were heated at 200° C. for 14 days at 50 psig (at 25° C.) of 100% H$_2$ and 225 psig of water vapor pressure. The fluoroborate anion was stable according to the $^{19}$F and $^{11}$B NMR of the acid solutions. In summary, the acids such as H$_2$B$_{12}$F$_{12}$.n H$_2$O have shown a stability toward hydrogen at the temperatures up to 200° C. Solid acid proton conductors based on CsHSO$_4$ degrade under a hydrogen atmosphere at these temperatures as indicated in U.S. Pat. No. 6,468,684.

EXAMPLE 9

Determination of Conductivity of H$_2$B$_{12}$F$_{12}$.nH$_2$O in Water

This example shows the conductivity of H$_2$B$_{12}$F$_{12}$.nH$_2$O as a liquid proton conductor from 20 to 200° C. at water vapor pressures above 250 torr. The acid was placed into a glass cell, which was connected to a water reservoir through a heated tube. The system was placed under vacuum and the temperature of the water reservoir was varied to change the water vapor pressure in the system, which was also measured by the vacuum gauge. The acid was a liquid (n was equal to 8) at temperatures between 20 to 200° C. and water vapor pressure above 250 torr. The conductivity of the liquid acid was determined using a Radiometer™ CDM210 conductivity meter and two-pole CDC741T conductivity cell. The conductivity cell was calibrated using KCl solutions. The results are shown in Table 1.

TABLE 1

Conductivity of liquid H$_2$B$_{12}$F$_{12}$•n H$_2$O compositions at water vapor pressure 200 torr.

| Temperature, ° C. | Relative Humidity, % | Conductivity, mS/cm |
|---|---|---|
| 120 | 14 | 355 |
| 152 | 5 | 307 |
| 163 | 4 | 283 |

The results in Table 1 show that the composition retains water at low humidity with little reduction in conductivity. The test is relevant to proton transfer between electrodes in an electrochemical device, e.g. a fuel cell. A base of at least 100-150 mS/cm minimum is desired, and these compositions significantly exceed that conductivity level.

The acid H$_2$B$_{12}$F$_{12}$.nH$_2$O retains enough water to remain in a liquid phase up to 200° C. at a water vapor pressure of only 250 torr. This property is dramatically different from the behavior of a similar chloroborate acid H$_2$B$_{12}$Cl$_{12}$.nH$_2$O, which solidifies above 145° C. and a water vapor pressure of 600 torr. The acid, H$_2$B$_{12}$F$_{12}$.nH$_2$O, also showed a higher conductivity (350 mS/cm) at lower humidity level (water vapor pressure 200 torr), than the conductivity of H$_2$B$_{12}$Cl$_{12}$.nH$_2$O (239 mS/sm at water vapor pressure 600 torr).

EXAMPLE 10

Mixture of Fluoroborate Acid and Anhydrous Phosphoric Acid

The purpose of this example is to demonstrate that mixtures of fluoroborate acid and anhydrous phosphoric acid form melts, which have high proton conductivity even under inert atmosphere. Solid mixtures $(H_3O)_2B_{12}F_{12}/2H_3PO_4$ (approximately 67 weight % of $(H_3O)_2B_{12}F_{12}$), $(H_3O)_2B_{12}F_{12}/4H_3PO_4$ (approximately 50 weight % of $(H_3O)_2B_{12}F_{12}$), and $(H_3O)_2B_{12}F_{12}/12H_3PO_4$ (approximately 25 weight % of $(H_3O)_2B_{12}F_{12}$) were prepared under an inert atmosphere. The mixtures were heated under an inert atmosphere at 60-140° C. and all formed clear solutions above 100° C. The 1:2 mixture melt crystallized at about 100° C. The conductivities of the mixtures (melts) under an inert atmosphere are shown in Table 2.

TABLE 2

Conductivity of the phosphoric acid/fluoroborate acid mixtures at 100° C. under inert atmosphere.

| Composition, molar ratio | Conductivity, mS/cm |
|---|---|
| 1 $(H_3O)_2B_{12}F_{12}$/12 $H_3PO_4$ | 190 |
| 1 $(H_3O)_2B_{12}F_{12}$/4 $H_3PO_4$ | 96 |
| 1 $H_2B_{12}F_{12}$•6$H_2O$/4 $H_3PO_4$ | 179 |

The conductivity of the mixtures (melts) increases dramatically by the addition of small amounts of water.

EXAMPLE 11

High Thermal Stability of the Phosphoric Acid/Fluoroborate Acid Mixtures

The purpose of this example is to determine the thermal stability of phosphoric acid/fluoroborate acid mixtures (melts). A mixture of $(H_3O)_2B_{12}F_{12}/2H_3PO_4$ (approximately 67 weight % of $(H_3O)_2B_{12}F_{12}$), was heated at 200° C. for 20 hours under an inert atmosphere. Only <0.2% of weight loss was observed and the anion was stable according to the $^{19}F$ NMR of the acid solution.

EXAMPLE 12

Oxygen Reduction Kinetics of Aqueous Solutions of the Fluoroborate Acid Mixtures with Phosphoric Acid The purpose of this example is to determine the oxygen reduction kinetics of aqueous solutions of the fluoroborate acid, and mixtures of fluoroborate acids with phosphoric acid.

Linear sweep voltammograms of aqueous acid solutions were recorded at 1400 rpm on a BAS rotating disc electrode apparatus with a CH Instruments Electrochemical Workstation potentiostat. The acid solutions were saturated with 1 atm of pure $O_2$ for at least 15 min before potential sweeps were made and $O_2$ purge was continued during the measurements. Several cyclic voltammetry scans were also applied between 1.0 and –0.2 V prior to collecting linear sweep data, to remove traces of electro-active impurities in the system. The working electrode was a Pt rotating disc electrode, which was polished, washed with distilled water, and dried before each new acid solution was measured. The reference was a Ag/AgCl electrode, and a Pt wire counter electrode was used.

Figure 5:
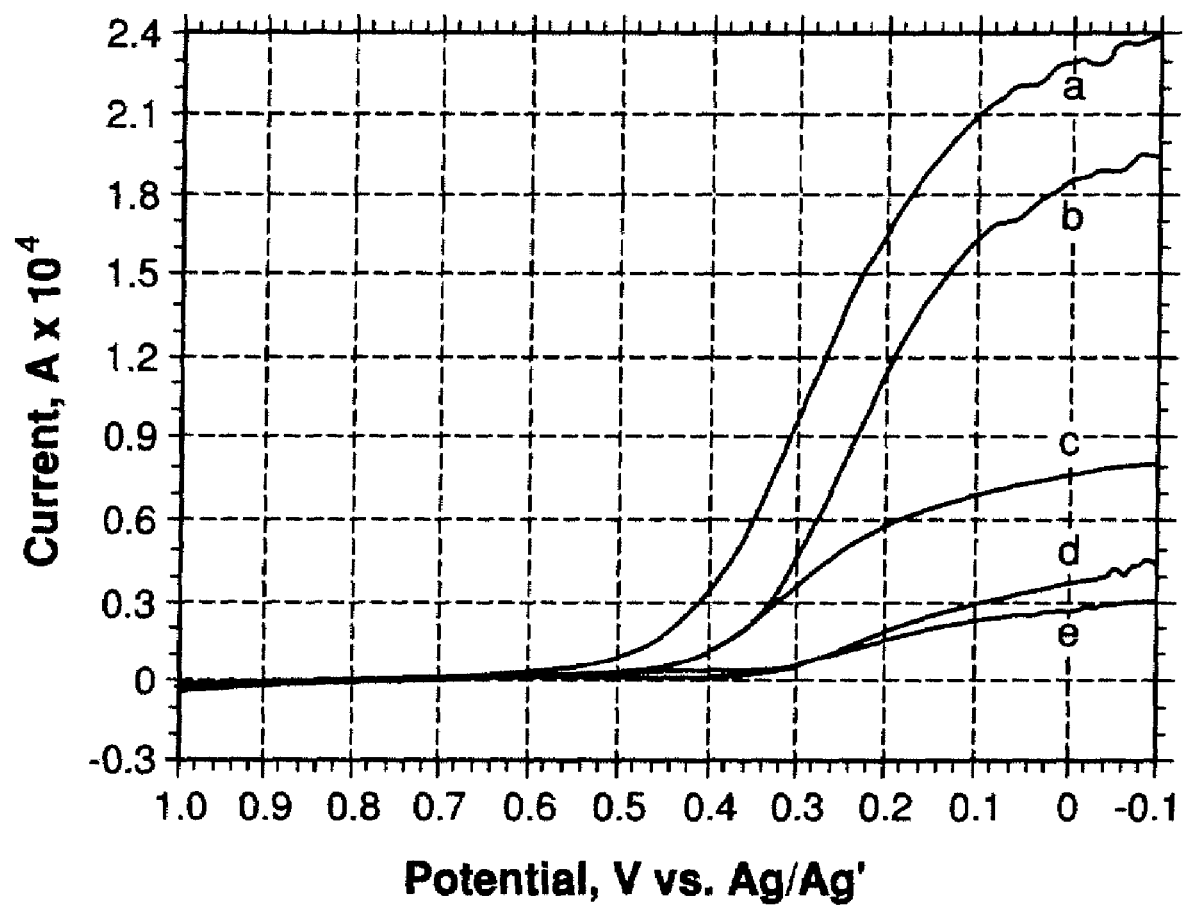
FIG. 5 shows rotating disc electrode (RDE) linear sweep voltammograms at 1400 RPM of aqueous acids: a) 18 wt % (0.5 M) solution of $H_2B_{12}F_{12}$; b) 5 wt % (0.5 M) solution of $H_3PO_4$; c) 60 wt % solution of a 1/1 mixture (by weight) of $H_3PO_4$ and $H_2B_{12}F_{12}$; d) 60 wt. solution % of $H_2SO_4$; and e) 60 wt % of $H_3PO_4$.

The graph, FIG. 5, shows better oxygen reduction kinetics for the hydrated fluorododecaborate acids and its mixtures with phosphoric acid than aqueous solutions of a neat phosphoric acid. The proton conducting electrolytes of this invention also provides a higher current at the same potential. Strong anion-absorption is indicated by a shift in oxygen reduction to increasingly negative potentials. This overpotential is associated with the greater distance required for electron transfer through the thicker absorption layer interface and interference of reactant absorption at the electrode.

Linear sweep voltammetry scans of relatively dilute aqueous solutions of $H_2B_{12}F_{12}$ and $H_3PO_4$, show a +0.1 V shift in $O_2$ reduction potential for the former, vis-à-vis $H_3PO_4$ indicating that the $B_{12}F_{12}^{2-}$ anion is less adsorbing on the platinum catalyst than phosphoric acid even in a relatively dilute solution. The effect is much larger for more concentrated solutions with the onset of $O_2$ reduction for both 60% $H_3PO_{4(aq)}$ and 60% $H_2SO_{4(aq)}$ being almost 0.2 V lower than in a 60% aqueous solution of a 1:1(wt. %) $H_2B_{12}F_{12}$ and $H_3PO_4$ mixture. The limiting current was almost three times higher for a 60% aqueous solution of a 1:1(wt. %) $H_2B_{12}F_{12}$ and $H_3PO_4$ mixture compared with the limiting current of 60% $H_3PO_{4(aq)}$ at the same potential, suggesting higher oxygen solubility in the solution containing the fluoroborate acid.

In summary, the solutions of fluoroborate acid proton conductors have better oxygen reduction kinetics on a platinum catalyst than solutions of neat phosphoric acid. The kinetics should result in electrochemical devices, e.g. fuel cells, with higher power density. Also, the resulting mixtures show much less adsorption on the platinum electrode than does neat phosphoric acid when used as the proton conducting electrolyte.

EXAMPLE 13

Preparation of Proton Conductive Solid Membranes from Fluoroborate Acids

The purpose of this example is to demonstrate the preparation of proton conductive solid membranes from fluoroborate acids as a proton conducting elelctrolyte.

Figure 6:
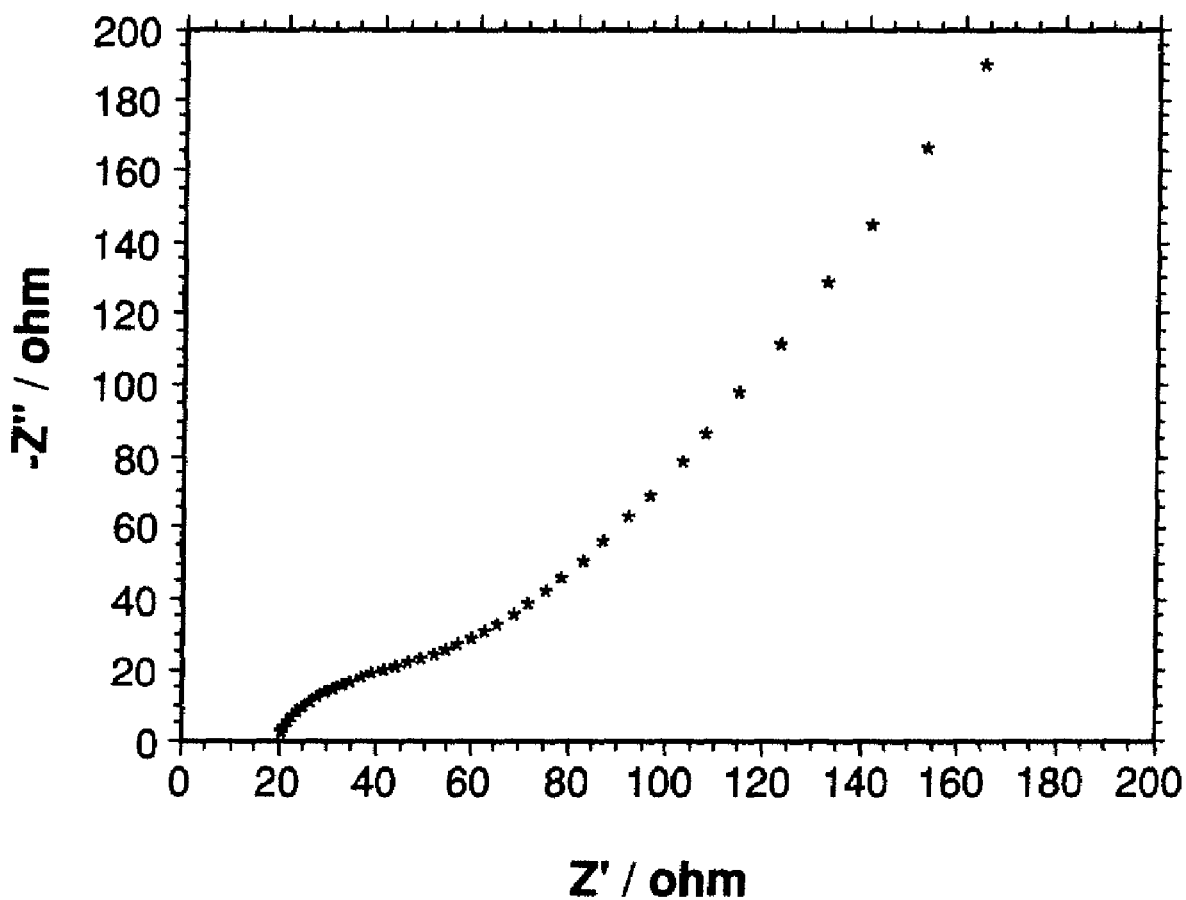
FIG. 6 shows an impedance plot of a glass fiber/fluoroborate acid proton conducting membrane in an electrochemical device at 182° C.

A glass fiber paper disk (about 125 μm thickness, diameter about 10 mm, 5.5 mg) was soaked for 15 minutes in a 30% solution of $(H_3O)_2B_{12}F_{12}$. When the disk was dried in the oven at 120° C. for two hours, a membrane with thickness 550 μm and 49 mg weight (about 90 wt % of the solid acid) was obtained. When a glass fiber disk was soaked in about 10% solution of $(H_3O)_2B_{12}F_{12}$ and the disk was dried at 120° C. for two hours, a membrane, 225 μm thick and weighing 18 mg, was obtained. To measure the conductivity, the membranes, dried at 120° C. for two hours, were pressed between the two gold disks, an alternating voltage (amplitude of 10 mV) in the frequency range 0.1 Hz to 0.1 MHz was applied to the membranes, and the complex impedance was measured and recorded in FIG. 6. Impedance spectroscopy was measured in accordance with X. Qian; N. Gu; Z. Cheng; X.Yang; E. Wang; S. Dong. *J. Solid State Electrochemistry*, 2001, 6, p. 8-15.

The membrane resistances were obtained by extrapolating the impedance data to the real axis on the high frequency side. The resistance of a 550 mm membrane was 30000Ω at 27° C. (conductivity was about 1.2 mS/cm), but the resistance at 182° C. was three orders of magnitude lower 23 Ω (conductivity was about 1.6 mS/cm).

EXAMPLE 14

This example demonstrates the preparation of proton conductive solid membranes from fluorinated closo-heteroborate acids. A mixture of compounds $Cs(CB_{11}F_{11}H)$ (0.3 g) and $[N(C_4H_5)_4][CB_{11}F_{11}H]$ (0.5 g) was dissolved in 30 ml of a 1:1 mixture of methanol and acetonitrile. The combined mixture was eluted through a column packed with Amberlyst-15 cation exchange resin and the liquid fraction was collected in its acidic form. 10 ml of DI water was added to the column fraction and the solvents were removed from the elute under vacuum. The remaining acid was dissolved in 5.0 ml of water. A glass fiber paper disk (about 125 μm thickness, diameter about 20 mm, and weight about 20 mg) was soaked in the solution of the fluorinated closo-heteroborate acid. After drying for two hours at 120° C., a solid disk containing about 50 wt % of the acid and about 50 wt % of the glass fibers was obtained. A solid disk containing about 90 wt % of the acid was obtained when the glass fiber paper disk was soaked in more concentrated acid solution and dried at 120° C. for two hours.

Figure 7:
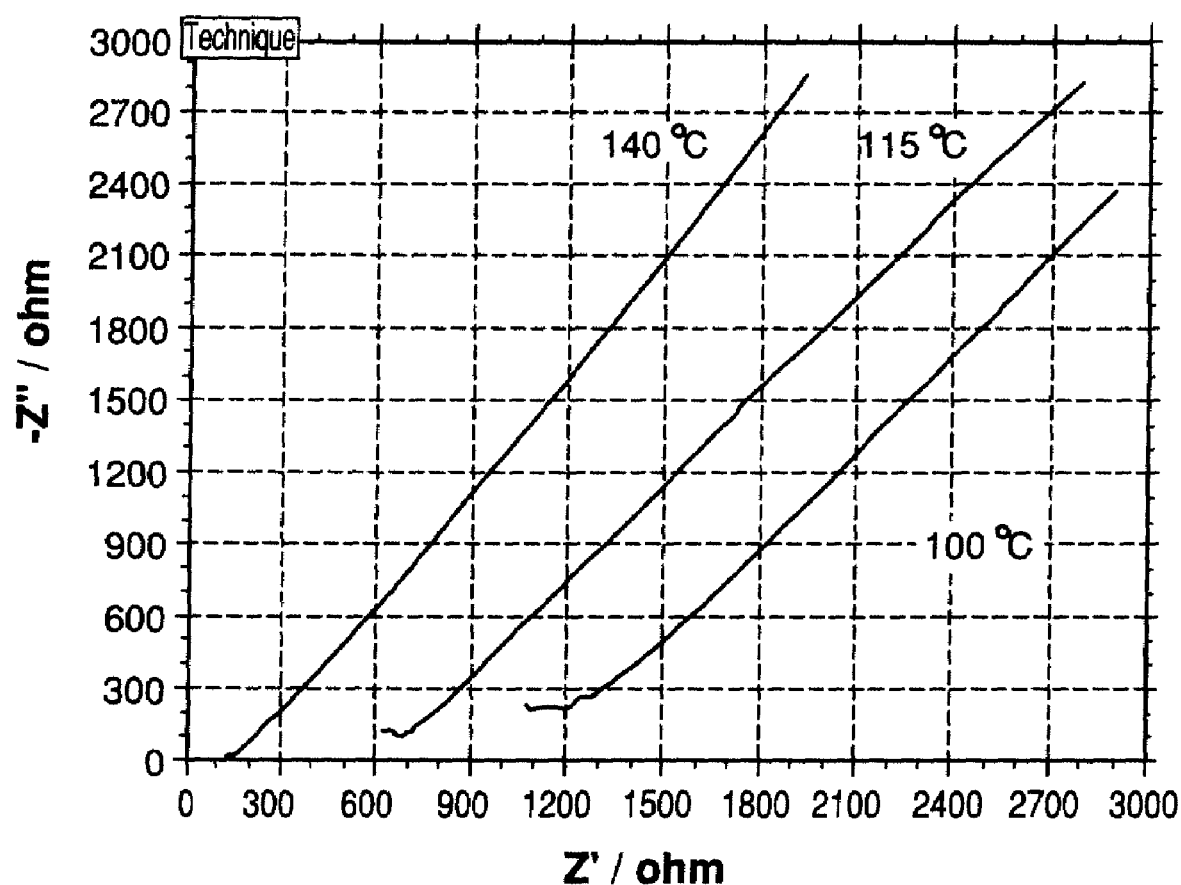
FIG. 7 shows impedance plots of an electrochemical device containing a proton conducting membrane composed of about 50 wt % glass fiber and about 50 wt % fluorinated heteroborate acid ($HCB_{11}F_{11}H \cdot nH_2O$).
Figure 8:
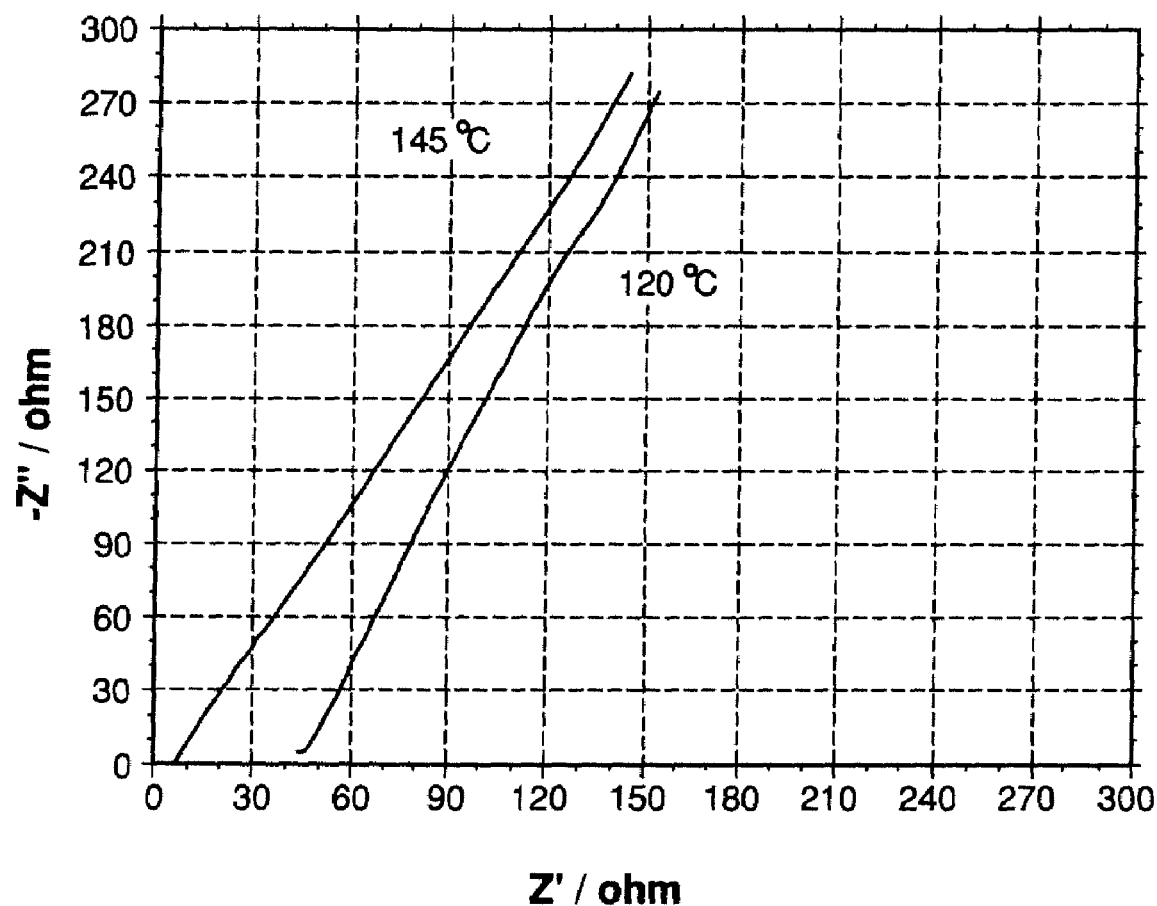
FIG. 8 shows impedance plots of an electrochemical device containing a proton conducting membrane composed of about 10 wt % glass fiber and about 90 wt % fluorinated heteroborate acid ($HCB_{11}F_{11}H \cdot nH_2O$).

A glass fiber disk containing fluorinated heteroborate acid $HCB_{11}F_{11}H.nH_2O$ was slightly pressed between two 15×0.5 mm stainless steel disks and dried for 24 hours at 120° C. The thickness of the solid membranes containing fluorinated heteroborate acid was 0.37 mm. The membrane assemblies were sealed into button cells. The cells were heated to various temperatures and the resistance of the membranes was determined by impedance spectroscopy methods. Complex impedance data was extrapolated to the real axis on the high frequency side, FIGS. 7 and 8. Conductivities of the membrane composed of about 50/50 wt % of the glass fibers and fluorinated closo-heteroborate acid were: 0.5 μS/cm at 22° C., 0.02 mS/cm at 100° C., 0.04 mS/cm at 112° C., and 0.1 mS/cm at 140° C. Conductivity of the membrane composed of about 10/90 wt % of the glass fibers and fluorinated closo-heteroborate acid was about the same at room temperature, but it was much higher at elevated temperatures: 0.7 μS/cm at 22° C., 0.47 mS/cm at 120° C., and 3.5 mS/cm at 145° C.

The examples show that advantages can be achieved by using the $H_aM_bQ.nH_2O$ polyhedral fluoroborate and fluoroheteroborate compositions as proton conducting electrolytes in electrochemical devices, including a fuel cell. Some embodiments of the proton conducting membranes of this invention are liquids having relatively low volatility and low viscosity; other embodiments are solids having low volatility and high viscosity, which if desired can function as a separator between the cathode and anode of an electrochemical device. Some embodiments have an affinity for water at any temperature, e.g., 0 to 250° C., 80-250° C., 120-220° C., or 150-200° C., and enable electrochemical devices to operate at any temperature, including 150-250° C. where the often-used platinum catalyst at an anode is less sensitive to CO poisoning. Many of the proton conducting electrolytes of this invention provide resistance to oxidation (by O2) and reduction (by H2) at operating temperatures; and/or weak adsorption to the platinum anode, enabling higher current densities to be obtained in some electrochemical devices. Further other embodiments of the proton conducting electrolyte of this invention are typically good solvents for oxygen enabling higher current densities to be obtained.

This invention has been described with reference to particular embodiments that are not meant to be limiting. Those skilled in the art will appreciate that modifications can be made to the disclosed embodiments without departing from the invention. Such equivalent variations are included within the scope of the invention. Any and all references, patents and patent applications cited herein are incorporated in their entireties by reference whether or not this or a similar statement follows each individual citation.

The invention claimed is:

1. An electrochemical device comprising a proton conducting medium said proton conducting medium comprising a proton conducting electrolyte comprising the formula:

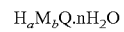

where H is a proton, M is a cation, Q is the fluoroborate or fluoroheteroborate anion, n is sufficient to form a liquid, a is a real number from 0.01 to 2 and b is a real number from 0 to 2, and when b is greater than 0, the ratio of b to a is less than 100 to 1, and a and b are chosen to render the formula electrically neutral; wherein the electrochemical device comprised a fuel cell.

2. The electrochemical device of claim 1, further wherein b is 0, and a is 1 or 2.

3. The electrochemical device of claim 1, further comprising a mixture of $H_aQ.nH_2O$, and $H_aM_bQ.nH_2O$.

4. The electrochemical device of claim 1, further comprising a mixture of $H_aQ.nH_2O$, and $H_aM_bQ.nH_2O$ in molar proportions ranging from 1:10 to 100:1.

5. The electrochemical device of claim 1, wherein M is selected from the group consisting of the consisting of the elements of Group 1, Group 2, Group 3, Group 13, and the Lanthanide series, and cobalt, zirconium, hafnium, nickel, and ammonium and organic substituted ammonium cations.

6. The electrochemical device of claim 1, wherein M is selected from the group consisting of tetraethylammonium, tetrabutylammonimum, triethylammonium, monomethylammonium, dimethylammonium, trimethylammonium, tetramethylammonium, imidazolium, and n-alkyl imidazolium.

7. The electrochemical device of claim 1 wherein M is selected from the group consisting of Li, Na, K, Cs, Mg, Ca, Ba, Al, Zr, or mixtures of those elements.

8. The electrochemical device of claim 1 wherein said proton conducting medium further comprises a second proton conducting electrolyte, said second proton conducting electrolyte being selected from the group consisting of anhydrous phosphoric acid, alkane sulfonic acid, fluoroalkanesulfonic acid, or sulfuric acid.

9. The electrochemical device of claim 8 wherein said polymer is selected from the group consisting of perfluorosulfonic acids, polyethylene oxide, polyimides, and polysulfones.

10. The electrochemical device of claim 8 wherein said polymer is selected from the group consisting of polyvinylpyridine, polyaniline, polybenzimidazole, and polybenzoxazoles.

11. The electrochemical device of claim 1, wherein said proton conducting medium further comprises a polymer.

12. The electrochemical device of claim 1 wherein said proton conducting medium further comprises a porous matrix.

13. The electrochemical device of claim 12 wherein said porous matrix comprises microglass fibers, silicon carbide, boron nitride, or porous carbon materials.

14. The electrochemical device of claim 1, wherein Q is selected from the group consisting of:
(i) the closo-borate anion of composition $(B_{12}F_xZ_{12-x})^{2-}$ or $(B_{10}F_xZ_{10-x})^{2-}$ where Z is H, Cl, Br or OR, where R is H, alkyl or fluoroalkyl, and x, on an average basis, ranges from 3 to 12 or from 2 to 10 respectively;
(ii) the closoammoniofluoroborate anion compositions of formula $((R'R''R''')NB_{12}F_xZ_{(11-x)})^{1-}$ or $((R'R''R''') NB_{10}F_xZ_{(9-x)})^{1-}$, where N is bonded to B and each of R', R'', R''' is independently selected from the group consisting of hydrogen, alkyl, cycloalkyl, aryl and a polymeric group; Z is H, Cl, Br, or OR, where R is H, alkyl or fluoroalkyl, and x, on an average basis, ranges from 0 to 11 or from 0 to 9 respectively; and (iii) the c/oso-monocarborate anion compositions of formula $(R''''CB_{11}F_xZ_{(11-x)})^{1-}$ or $(R''''CB_9F_xZ_{(9-x)})^{1-}$, where R'''' is bonded to C and is selected from the group consisting of hydrogen, alkyl, cycloalkyl, aryl, and a polymeric group, Z is H, Cl, Br, or OR, where R is H, alkyl or fluoroalkyl, and x, on an average basis, ranges from 0 to 11 or from 0 to 9 respectively.

15. The electrochemical device of claim 1 further comprising a hydrogen anode and an oxygen cathode.

16. The electrochemical device of claim 1 wherein said fuel cell comprises a liquid proton conducting electrolyte.

17. The electrochemical device of claim 1, wherein Q is selected from the group consisting of:

(i) the c/oso-borate anion of composition $(B_{12}F_xZ_{12-x})^{2-}$ or $(B_{10}F_xZ_{10-x})^{2-}$ where Z is H, Cl, Br or OR, where R is H, alkyl or fluoroalkyl, and x, on an average basis, ranges from 3 to 12 or from 2 to 10 respectively.

18. A fuel cell device comprising: a hydrogen anode, an oxygen cathode and a liquid proton conducting medium said proton conducting medium comprising a proton conducting electrolyte comprising the formula:

$$H_aM_bQ.nH_2O$$

where H is a proton, M is a cation, Q is the fluoroborate or fluoroheteroborate anion, n is a number from 1 to 1000, a is a real number from 0.01 to 2 and b is a real number from 0 to 2, and when b is greater than 0, the ratio of b to a is less than 100 to 1, and a and b are chosen to render the formula electrically neutral.

19. The fuel cell device of claim 18 wherein the medium is supported by or blended with a polymeric matrix.

20. The fuel cell device of claim 18 wherein Q comprises $B_{12}F_xZ_{12-x}$ wherein Z comprises H, and x, on an average basis, ranges from 3 to 12.

21. The fuel cell device of claim 18 wherein the medium further comprises $O_2$.

* * * * *

UNITED STATES PATENT AND TRADEMARK OFFICE
CERTIFICATE OF CORRECTION

PATENT NO. : 7,591,964 B2 Page 1 of 1
APPLICATION NO. : 11/952437
DATED : September 22, 2009
INVENTOR(S) : Sergei Vladimirovich Ivanov, William Jack Casteel, Jr. and Guido Peter Pez It is certified that error appears in the above-identified patent and that said Letters Patent is hereby corrected as shown below:

Column 19, Line 18

In claim 17 delete "c/oso" and insert --closo--

Signed and Sealed this

Third Day of November, 2009

David J. Kappos
*Director of the United States Patent and Trademark Office*